(12) United States Patent
Lebofsky et al.

(10) Patent No.: US 8,586,723 B2
(45) Date of Patent: Nov. 19, 2013

(54) GENOMIC MORSE CODE

(75) Inventors: Ronald Lebofsky, Toronto (CA); Aaron Bensimon, Antony (FR); Pierre Walrafen, Montrouge (FR)

(73) Assignees: Institut Pasteur, Paris (FR); Genomic Vision, Paris (FR)

( * ) Notice: Subject to any disclaimer, the term of this patent is extended or adjusted under 35 U.S.C. 154(b) by 917 days.

(21) Appl. No.: 12/440,134

(22) PCT Filed: Sep. 5, 2007

(86) PCT No.: PCT/EP2007/059299
§ 371 (c)(1),
(2), (4) Date: Aug. 7, 2009

(87) PCT Pub. No.: WO2008/028931
PCT Pub. Date: Mar. 13, 2008

(65) Prior Publication Data
US 2010/0041036 A1 Feb. 18, 2010

Related U.S. Application Data

(63) Continuation of application No. 11/516,673, filed on Sep. 7, 2006, now Pat. No. 7,985,542.

(51) Int. Cl.
*C12N 15/11* (2006.01)
*C07H 21/04* (2006.01)
*C07K 16/00* (2006.01)

(52) U.S. Cl.
USPC ........ 536/24.3; 435/6.11; 435/7.1; 530/387.1

(58) Field of Classification Search
None
See application file for complete search history.

(56) References Cited

U.S. PATENT DOCUMENTS

| | | | |
|---|---|---|---|
| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 5,143,854 | A | 9/1992 | Pirrung |
| 5,405,783 | A | 4/1995 | Pirrung |
| 5,445,934 | A | 8/1995 | Fodor |
| 5,800,992 | A | 9/1998 | Fodor et al. |
| 6,040,138 | A | 3/2000 | Lockhart et al. |
| 7,985,542 | B2 * | 7/2011 | Lebofsky et al. ............ 435/6.1 |
| 2004/0235014 | A1 * | 11/2004 | Nadel et al. .............. 435/6 |
| 2004/0248107 | A1 * | 12/2004 | Sokolova et al. ............ 435/6 |
| 2004/0248144 | A1 * | 12/2004 | Mir .................. 435/6 |

FOREIGN PATENT DOCUMENTS

WO WO 96/14839 5/1996

OTHER PUBLICATIONS

Molecular Biology Reagents/Protocols 1992, United States Biochemical Corporation, 1991, Cleveland, Ohio, p. 618.*
Ahern, The Scientist 9 (15), 20 (1995).*
Anglana et al., 2003, "Dynamics of DNA replication in mammalian somatic cells: nucleotide pool modulates origin choice and interorigin spacing," Cell 114, 385-394.
Bensimon et al., 1994, "Alignment and sensitive detection of DNA by a moving interface," Science 265, 2096-2098.
Berezney et al., 2000, "Heterogeneity of eukaryotic replicons, replicon clusters, and replication foci," Chromosoma 108, 471-484.
Blow et al., 2005, "Preventing re-replication of chromosomal DNA," Nat. Rev. Mol. Cell Biol. 6, 476-486.
Brewer et al., 1993, "Initiation at closely spaced replication origins in a yeast chromosome,". Science 262, 1728-1731.
Cvetic et al., 2005, "Eukaryotic origins of DNA replication: could you please be more specific?", Semin. Cell Dev. Biol. 16, 343-353.
DePamphilis, M.L., 1999, "Replication origins in metazoan chromosomes: fact or fiction?", Bioessays 21, 5-16.
Dershowitz et al., 1993, "The effect on chromosome stability of deleting replication origins," Mol. Cell. Biol. 13, 391-398.
Edenberg et al., 1975, "Eukaryotic chromosome replication," Ann. Rev. Genet., 9, 245-284.
Edwards et al., 2002, "MCM2-7 complexes bind chromatin in a distributed pattern surrounding the origin recognition complex in Xenopus egg extracts," J. Biol. Chem. 277, 33049-33057.
Friedman et al., 1997, "Replication profile of *Saccharomyces cerevisiae* chromosome VI," Genes Cells 2, 667-678.
Gilbert, D.M., 2004, "In search of the holy replicator," Nat. Rev. Mol. Cell Biol. 5, 848-855.

(Continued)

*Primary Examiner* — James Martinell
(74) *Attorney, Agent, or Firm* — Foley & Lardner LLP

(57) ABSTRACT

The present invention relates to a method of detection of the presence of at least one domain of interest on a macromolecule to test, wherein said method comprises the following steps: a) determining beforehand at least two target regions on the domain of interest, designing and obtaining corresponding labeled probes of each target region, named set of probe of the domain of interest, the position of these probes one compared to the others being chosen and forming the specific signature of said domain of interest on the macromolecule to test; b) after spreading of the macromolecule to test on which the probes obtained in step a) are bound, detection of the position one compared to the others of the probes bound on the linearized macromolecule, the detection of the signature of a domain of interest indicating the presence of said domain of interest on the macromolecule to test, and conversely the absence of detection of signature or part of signature of a domain of interest indicating the absence of said domain or part of said domain of interest on the macromolecule to test.

6 Claims, 7 Drawing Sheets

(56) References Cited

OTHER PUBLICATIONS

Hand et al., 1973, "DNA replication: direction and rate of chain growth in mammalian cells," J. Cell Biol. 58, 410-418.
Hyrien et al., 2003, "Paradoxes of eukaryotic DNA replication: MCM proteins and the random completion problem," Bioessays 25, 116-125.
Jun et al., 2004, "Persistence length of chromatin determines origin spacing in Xenopus early-embryo DNA replication: quantitative comparisons between theory and experiment," Cell Cycle 3, 223-229.
Lebofsky et al., 2005, "DNA replication origin plasticity and perturbed fork progression in human inverted repeats," Mol. Cell. Biol. 25, 6789-6797.
Lengronne et al., 2002, "The yeast CDK inhibitor Sic1 prevents genomic instability by promoting replication origin licensing in late G(1)," Mol. Cell 9, 1067-1078.
Lucas et al., 2000, "Mechanisms ensuring rapid and complete DNA replication despite random initiation in Xenopus early embryos," J. Mol. Biol. 296, 769-786.
Lucas et al., 2003, "The dynamics of chromosome replication in yeast," Curr. Top. Dev. Biol. 55, 1-73.
MacAlpine et al., 2004, "Coordination of replication and transcription along a Drosophila chromosome," Genes Dev. 18, 3094-3105.
Marheineke et al., 2004, "Control of replication origin density and firing time in Xenopus egg extracts: role of a caffeine-sensitive, ATR-dependent checkpoint," J. Biol. Chem. 279, 28071-28081.
Newlon et al., 1991, "Analysis of a circular derivative of *Saccharomyces cerevisiae* chromosome III: a physical map and identification and location of ARS elements," Genetics 129, 343-357.
Norio et al., 2005, "Progressive activation of DNA replication initiation in large domains of the immunoglobulin heavy chain locus during B cell development," Mol. Cell 20, 575-587.
Pasero et al., 2002, "Single-molecule analysis reveals clustering and epigenetic regulation of replication origins at the yeast rDNA locus," Genes Dev. 16, 2479-2484.
Poloumienko et al., 2001, "Completion of replication map of *Saccharomyces cerevisiae* chromosome III," Mol. Biol. Cell 12, 3317-3327.
Raghuraman et al., 1997, "Cell cycle-dependent establishment of a late replication program," Science 276, 806-809.
Raghuraman et al., 2001, "Replication dynamics of the yeast genome," Science 294, 115-121.
Ritzi, 1998, "Human minichromosome maintenance proteins and human origin recognition complex 2 protein on chromatin," J. Biol. Chem. 273, 24543-24549.
Rothstein et al., 2000, "Replication fork pausing and recombination or gimme a break," Genes Dev. 14, 1-10.
Santocanale et al., 1996, "ORC- and Cdc6-dependent complexes at active and inactive chromosomal replication origins in *Saccharomyces cerevisiae*," EMBO J. 15, 6671-6679.
Santocanale et al., 1999, "Activation of dormant origins of DNA replication in budding yeast," Genes Dev. 13, 2360-2364.
Schwob, E., 2004, "Flexibility and governance in eukaryotic DNA replication," Curr. Opin. Microbiol. 7, 680-690.
Shechter et al., 2004, "ATR and ATM regulate the timing of DNA replication origin firing," Nat. Cell Biol. 6, 648-655.
Shimada et al., 2002, "ORC and the intra-S-phase checkpoint: a threshold regulates Rad53p activation in S phase," Genes Dev. 16, 3236-3252.
Shirahige et al., 1993, "Location and characterization of autonomously replicating sequences from chromosome VI of *Saccharomyces cerevisiae*," Mol. Cell. Biol. 13, 5043-5056.
Sorensen et al., 2004, "ATR, Claspin and the Rad9- Rad1-Hus1 complex regulate Chk1 and Cdc25A in the absence of DNA damage," Cell Cycle 3, 941-945.
Syljuasen et al., 2005, "Inhibition of human Chk1 causes increased initiation of DNA replication, phosphorylation of ATR targets, and DNA breakage," Mol. Cell. Biol. 25, 3553-3562.
Tanaka et al., 2002, "Deregulated G1-cyclin expression induces genomic instability by preventing efficient pre-RC formation," Genes Dev. 16, 2639-2649.
Todorovic, V., 2005, "Human origins of DNA replication selected from a library of nascent DNA," Mol. Cell 19, 567-575.
Vujcic et al., 1999, "Activation of silent replication origins at autonomously replicating sequence elements near the HML locus in budding yeast," Mol. Cell. Biol. 19, 6098-6109.
Walter et al., 1997, "Regulation of replicon size in Xenopus egg extracts," Science 275, 993-995.
Wyrick et al., 2001, "Genome-wide distribution of ORC and MCM proteins in *S. cerevisiae*: high-resolution mapping of replication origins," Science 294, 2357-2360.
Yamashita et al., 1997, "The efficiency and timing of initiation of replication of multiple replicons of *Saccharomyces cerevisiae* chromosome VI," Genes Cells 2, 655-665.
International Search Report issued on Dec. 14, 2007 for application No. PCT/EP2007/059299.
Lebofsky et al., "DNA Replication Origin Interference Increases the Spacing between Initiation Events in Human Cells," *Molecular Biology of the Cell*, vol. 17, pp. 5337-5345, Dec. 2006.
Michalet et al., "Dynamic Molecular Combing: Stretching the Whole Human Genome for High-Resolution Studies," *Science*, vol. 277, pp. 1518-1523, Sep. 1997.
Office Action issued on Dec. 28, 2009 by the Examiner in U.S. Appl. No. 11/516,673.
Office Action issued on Nov. 5, 2009 by the Examiner in U.S. Appl. No. 11/516,673.
Office Action issued on May 22, 2009 by the Examiner in U.S. Appl. No. 11/516,673.
Office Action issued on Oct. 2, 2008 by the Examiner in U.S. Appl. No. 11/516,673.
Office Action issued on Jun. 11, 2008 by the Examiner in U.S. Appl. No. 11/516,673.

\* cited by examiner

• ▬ •   « R » in Morse Code

Code based on spacing a)

Code based on colour b)

Redundant Code c)

Figure 7

```
aacbbcb
 acbbcba
  cbbcbaa
   bbcbaac
    bcbaacb
     cbaacbb
      baacbbc
       aacbcc
``` aacbbcbaacbbcc

---

```
aaaaaaabaaaaaacaaaaabbaaaaabcaaaaacbaaaaaccaaaababaaaabacaaaabbbaaaab
bcaaaabcbaaaabccaaaacabaaaacacaaaacbbaaaacbcaaaaccbaaaacccaaabaabaaab
aacaaababbaaababcaaabacbaaabaccaaabbabaaabbacaaabbbbaaabbbcaaabbcbaaa
bbccaaabcabaaabcacaaabcbbaaabcbcaaabccbaaabcccaaacaabaaacaacaaacabbaa
acabcaaacacbaaacaccaaacbabaaacbacaaacbbbaaacbbcaaacbcbaaacbccaaaccaba
aaccacaaaccbbaaaccbcaaacccbaaaccccaabaabbaabaabcaabaacbaabaaccaababab
aababacaababbbaababbcaababcbaababccaabacabaabacacaabacbbaabacbcaabacc
baabacccaabbaacaabbabbaabbabcaabbacbaabbaccaabbbabaabbbacaabbbbbaabbb
bcaabbbcbaabbbccaabbcabaabbcacaabbcbbaabbcbcaabbccbaabbcccaabcaacaabc
abbaabcabcaabcacbaabcaccaabcbabaabcbacaabcbbbaabcbbcaabcbcbaabcbccaab
ccabaabccacaabccbbaabccbcaabcccbaabccccaacaacbaacaaccaacababaacabacaa
cabbbaacabbcaacabcbaacabccaacacabaacacacaacacbbaacacbcaacaccbaacaccca
acbabbaacbabcaacbacbaacbaccaacbbabaacbbacaacbbbbaacbbbcaacbbcbaacbbcc
aacbcabaacbcacaacbcbbaacbcbcaacbccbaacbcccaaccabbaaccabcaaccacbaaccac
caaccbabaaccbacaaccbbbaaccbbcaaccbcbaaccbccaacccabaacccacaacccbbaaccc
bcaaccccbaaccccabababbabababcababacbababaccababbacabababbbababbbcabab
bcbababbccababcacababcbbababcbcababccbababcccabacabbabacabcabacacbaba
caccabacbacabacbbbabacbbcabacbcbabacbccabaccacabaccbbabaccbcabaccccbab
acccabbabbbabbabbcabbabcbabbabccabbacacabbacbbabbacbcabbaccbabbaccca
bbbabcabbbacbabbbaccabbbbacabbbbbbabbbbbcabbbbcbabbbbccabbbcacabbbcbb
abbbcbcabbbccbabbbcccabbcabcabbcacbabbcaccabbcbacabbcbbbabbcbbcabbcbc
babbcbccabbccacabbccbbabbccbcabbcccbabbccccabcabcbabcabccabcacacabcac
bbabcacbcabcaccbabcacccabcbacbabcbaccabcbbacabcbbbbabcbbcabcbbcbabcb
bccabcbcacabcbcbbabcbcbcabcbccbabcbcccabccacbabccaccabccbacabccbbbabc
cbbcabccbcbabccbccabcccacabcccbbabcccbcabcccbabcccccacacacbacacaccac
acbbbacacbbcacacbcbacacbccacaccbbacaccbcacacccbacaccccacbacbbacbacbca
cbaccbacbacccacbbaccacbbbbbacbbbbcacbbbcbacbbbccacbbcbbacbbcbcacbbccb
acbbcccacbcaccacbcbbbacbcbbcacbcbcbacbcbccacbccbbacbccbcacbcccbacbccc
caccaccbaccacccaccbbbbaccbbbcaccbbcbaccbbccaccbcbbaccbcbcaccbccbaccbc
ccacccbbbacccbbcacccbcbacccbccacccbbacccbcacccccbacccccbbbbbbbbbcbbb
bbccbbbbcbcbbbbcccbbbcbbcbbbbcbccbbbccbcbbbcccccbbcbbccbbcbcbcbbcbcccbb
ccbccbbcccbcbbccccbcbcbccbcbccccbccbcccbcccccccaaaaaa
```

GENOMIC MORSE CODE

FIELD OF THE INVENTION

The present invention relates to a method of detection of the presence of at least one domain of interest on a macromolecule to test, wherein said method comprises the following steps:
  a) determining beforehand at least two target regions on the domain of interest, designing and obtaining corresponding labeled probes of each target region, named set of probe of the domain of interest, the position of these probes one compared to the others being chosen and forming the specific signature of said domain of interest on the macromolecule to test;
  b) after spreading of the macromolecule to test on which the probes obtained in step a) are bound, detection of the position one compared to the others of the probes bound on the linearized macromolecule, the detection of the signature of a domain of interest indicating the presence of said domain of interest on the macromolecule to test, and conversely the absence of detection of signature or part of signature of a domain of interest indicating the absence of said domain or part of said domain of interest on the macromolecule to test.

More particularly, the invention relates to a kit for the detection of the presence of at least two domain of interest on a macromolecule comprising at least two set of three probes, each set of probes being capable of binding specifically on one domain wherein the binding of one set of at least three probes on the macromolecule forms a sequence of at least two codes chosen between a group of at least two different codes (for example "dots" and "dashes"), said group being identical for all the domains, said sequence of codes being specific of one domain and being the signature of said domain.

BACKGROUND

The study of the macromolecules, in particular biological ones (more specifically DNA), often requires to mark up precisely some domains, either for "cartographic" purposes, i.e. to study the spatial organization of these domains, or for the purpose of locating the position, on the macromolecule, of a reaction or a set of chemical or biochemical reactions.

Methods which allow observation of spatial organization of DNA sequences (Fiber-FISH, Molecular Combing, . . . ) require in numerous applications that some regions are landmarked, i.e. marked in a way that allows identification of specific regions through some detection technique. This is the case for cartographic applications, where the main issue addressed is the relative position of several regions, as well as applications where a biological phenomenon is studied in one (several) specific locus (loci). Domains can then be identified by specific markers, in fact generally probes of DNA complementary to the sequences of interest (named domain of interest). These markers can be detected, for example by fluorescence microscopy, autoradiography, etc.

Whatever the detection technique used, the usual method for landmarking consists in synthesizing probes, i.e. sequences complementary to the regions of interest coupled to elements which allow detection (fluorochromes, radioelements, . . . ). To distinguish several regions, the main method is to design probes which can be distinguished based on their intrinsic properties such as their length or the nature of the detectable elements (typically, fluorochromes of different colours). In this case, probes are distinguishable because, even when detected individually they can be identified: they are of different nature.

This approach rapidly reaches its limits when it comes to distinguish a great number of regions: length of the probes suffers technical constraints and the number of different detectable elements is often limited.

Indeed, it is often necessary to mark several domains simultaneously in a differentiable way. The efforts to develop differentiable markers primarily consisted in multiplying the markers of different "nature", i.e. which can be differentiated individually by the method of detection used: coupling of fluorochromes of different spectra in microscopy with fluorescence, use of different probe lengths in microscopy with fluorescence and autoradiography. The principal limit with these approaches is that the number of different markers thus obtained is limited. In addition, simultaneous detection of markers of different nature generally obliges to use delicate and long to implement methods of acquisition.

SUMMARY OF THE INVENTION

The invention relates to a method of detection of the presence and/or position of at least one domain of interest on a macromolecule to test, wherein said method comprises the following steps:
  a) determining beforehand at least two target regions on the domain of interest, designing and obtaining corresponding labeled probes of each target region, named set of probe of the domain of interest, the position of these probes one compared to the others being chosen and forming the specific signature of said domain of interest on the macromolecule to test;
  b) after spreading of the macromolecule to test on which the probes obtained in step a) are bound, detection of the position one compared to the others of the probes bound on the linearized macromolecule, the detection of the signature of a domain of interest indicating the presence of said domain of interest on the macromolecule to test, and conversely the absence of detection of signature or part of signature of a domain of interest indicating the absence of said domain or part of said domain of interest on the macromolecule to test.

In an embodiment, the macromolecule is nucleic acid, particularly DNA, more particularly double strand DNA.

In an additional embodiment, the set of probes comprises in addition two probes (probe 1 or probe 2), each probe capable of binding on a different extremity of the domain of interest, the reading of the signal of one of said probe 1 or probe 2 associated with its consecutive probe in the domain of interest, named "extremity probe couple of start or end" allowing to obtain an information of start or end of reading.

In an additional embodiment, the invention relates to a kit for the detection of the presence of at least two domain of interest on a macromolecule comprising at least two set of three probes, each set of probes being capable of binding specifically on one domain wherein the binding of one set of at least three probes on the macromolecule forms a sequence of at least two codes chosen between a group of at least two different codes (for example "dots" and "dashes"), said group being identical for all the domains, said sequence of codes being specific of one domain and being the signature of said domain.

(A) Three types of replication signals on combed DNA that indicate an origin. Initiation occurs before the labeling periods, during the IdU pulse (blue), and during the CldU pulse (red) giving rise to the signals shown in (i), (ii), and (iii) respectively. In all three cases, the midpoint of the tracks is assumed to be the site of initiation.

(B) Hybridization strategies on combed DNA. Two probes of equal length but detected with different colors (i) or two probes of different length detected with the same color (ii) are hybridized to visualize a genomic region of interest. Alternatively, gaps between probe sets can be used to provide the same information. In (iii), four short probes are hybridized giving rise to three informative gaps. Gap 3 allows the molecule to be oriented during breakage (iv, v). DNA breaks are denoted by a pair of vertical solid lines.

(C) Genomic Morse Code (GMC) covering 1.356 Mb in human chromosome 14q11.2. The linear patterns of the first four symbols in Morse Code, A, B, C and D, are provided. GMC comprises these four symbols, each symbol represented by a set of probes. Probes are shown in green. Coding gaps are short gap and long gap. Start gap and end gap were included to help orient symbols when DNA breaks. Symbols are separated by space gaps. Probe and gap sizes in kb are given above each respectively.

(D) Examples of observed initiation events in the GMC region. White arrows indicate the initiation site. For fibers 2, 7, 8, and 13, GMC is still decodable even though all probes pertaining to a symbol are not present. Initiation events flanking the symbols were mapped when one of the adjacent symbols was decoded (molecules 1, 5, 11, and 14) or space gap information was available (molecules 4 and 10). (bar=100 kb)

Figure 2:
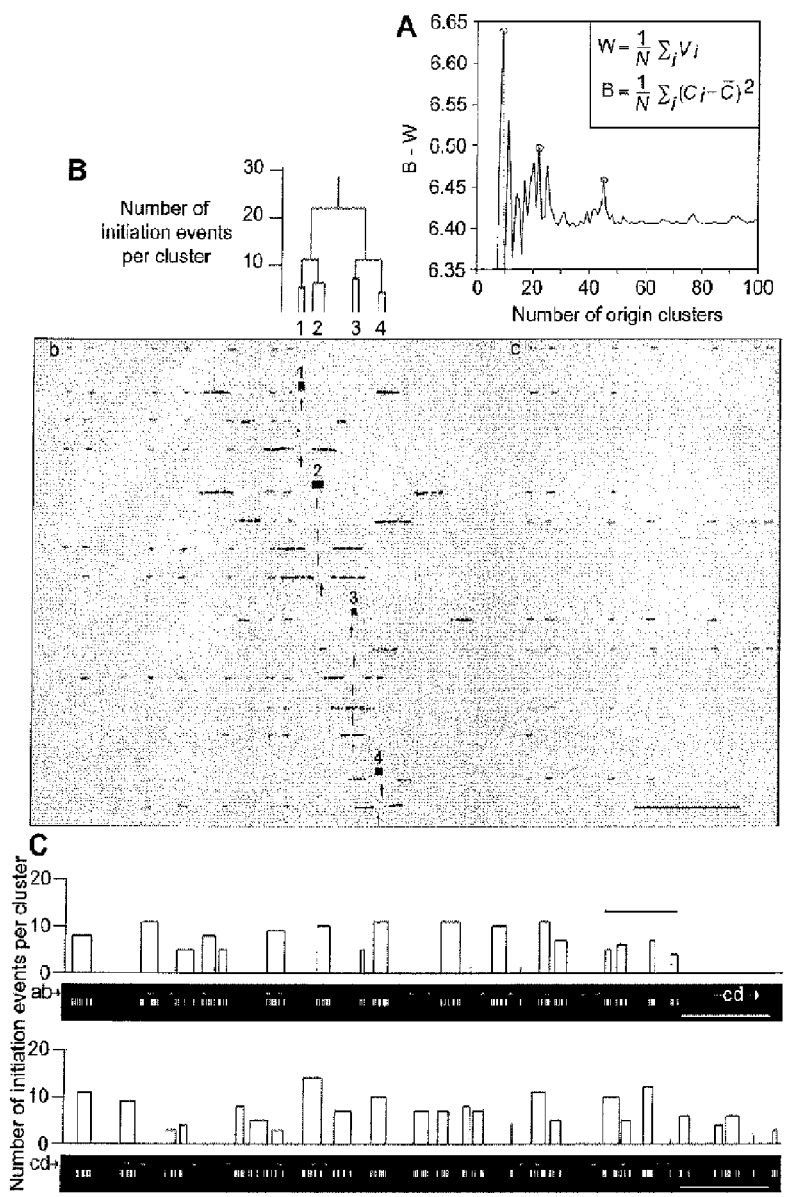

FIG. 2 shows initiation zone identification by cluster analysis.

(A) Defining ideal clusters. Equations for within variance (W) and between variance (B) are shown in the inset. For W, N is the number of clusters and Vi is the variance of cluster i. For B, Ci is the centroid of cluster i and C is the mean of all the centroids in a cluster set. Plotting B-W as a function of the number of clusters revealed maximal values when the data was divided into 9 (blue circle), 22 (green circle), and 45 (red circle) groups.

(B) The breakdown of one cluster into its components when 9 (blue line), 22 (green line) and 45 (red line) partitions are applied to the data. Regions underneath the red lines represent initiation zones, which are illustrated by the white boxes above the molecules. White arrows indicate the initiation site. (bar =100 kb).

(C) Distribution of initiation zones in the GMC region. The horizontal red lines denote zone size and position. Vertical white lines designate positions of all the 307 initiation sites mapped. Zones that contain less than 4 data points are marked by a horizontal grey line instead of a red one and are not considered in subsequent analyses. The cluster in panel B of this figure is indicated by an asterisk. (bar=100 kb).

Figure 3:
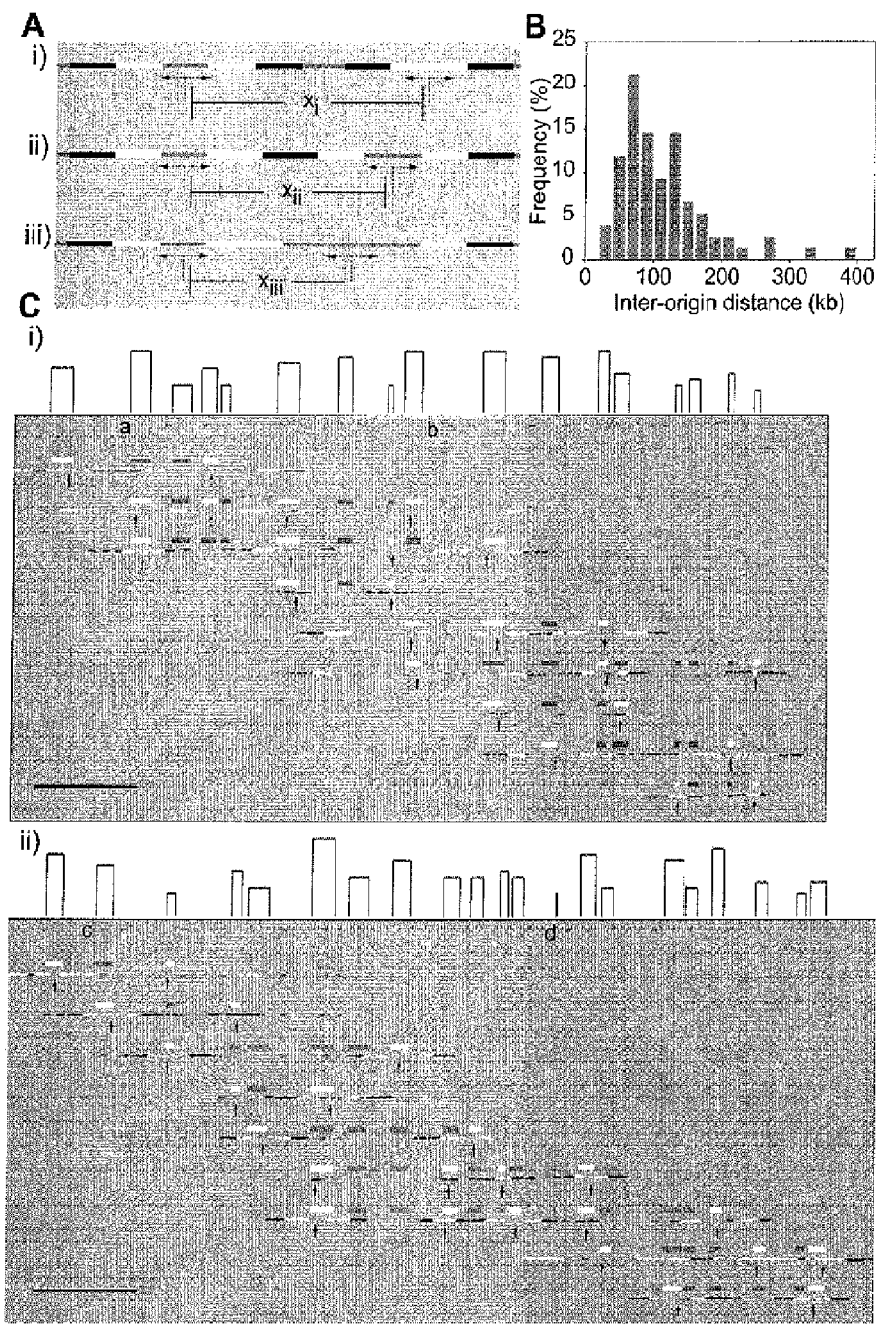

FIG. 3 shows spatio-temporal analysis of functional origins.

(A) Replication signals that provide inter-origin distances (X). In (i), the replication tracks from two initiation sites remain separate. In (ii) and (iii), oncoming forks merge during the IdU and CldU pulses respectively.

(B) Histogram showing the frequency of measured inter-origin distances.

(C) Examples of molecules with at least two initiation events in symbols A, B (i) and C, D (ii). White arrows indicate the initiation site. Initiation zones are marked by horizontal red lines. For individual molecules, the initiation zone from which an origin fires is indicated by a white box. Dark boxes designate silent initiation zones. (bar=100 kb)

Figure 4:
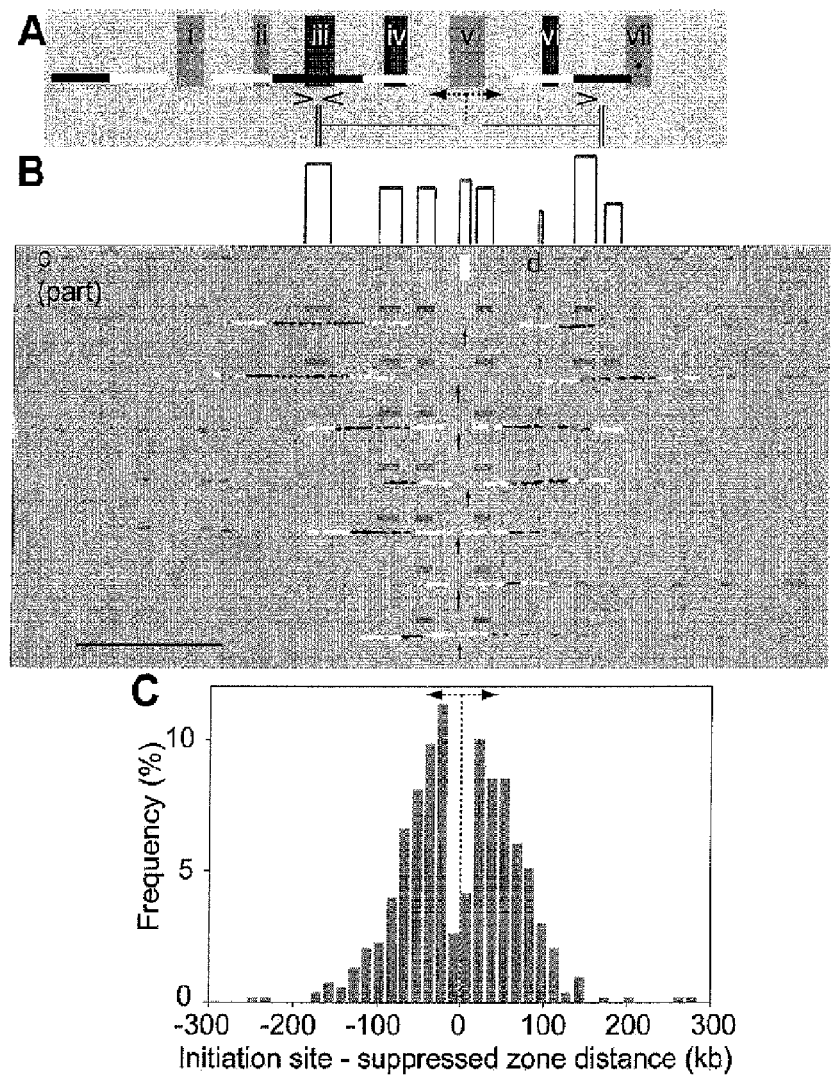

FIG. 4 shows origin interference based on fork extension.

(A) Forks elongating from the active origin in zone (v) cover the region bounded by the vertical line pairs. The termination of the leftward moving fork is observed (inverted open triangles). Initiation zones (i) and (ii) are not interfered with, as the fork from the origin in question does not extend to its boundaries. Zones (iii), (iv) and (vi) are suppressed as the fork passively replicates their entire lengths. The rightward moving fork penetrates zone (vii), but does not reach its centroid (black dot). This zone is not included in the origin interference data. Grey rectangles designate initiation zones and dark grey rectangle designate suppressed initiation zones.

(B) Examples of molecules that display origin interference. The initiation zones relevant to this figure are illustrated by the horizontal red lines. The white box marks the initiation zone from which origins fire (white arrows). Dark boxes indicate initiation zones that are suppressed due to fork extension. (bar=100 kb).

(C) Histogram showing the frequency of distances between an initiation event and zones interfered with. Zones that were suppressed by centromeric and telomeric moving forks are represented by negative and positive values respectively.

Figure 5:
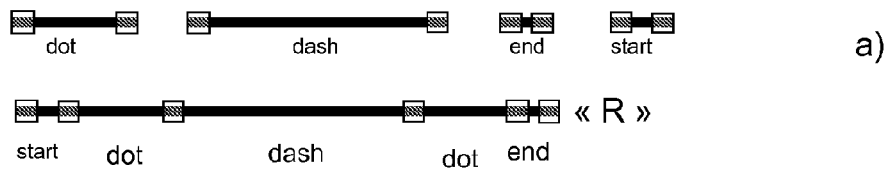
Figure 5:
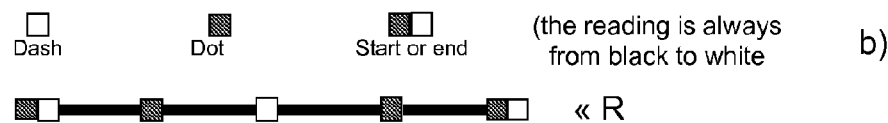
Figure 5:
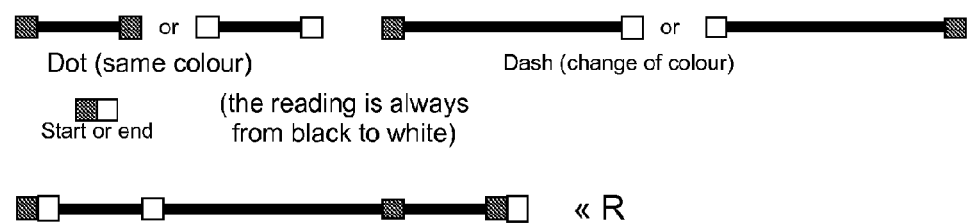

FIG. 5 shows three types of codes

A: code based on spacing between consecutives probes

B: code based on label (more particularly color)

C: redundant code based on label (color)+spacing between consecutives probes

Three types of coding. The probes are illustrated by a short segment of color. These probes can for example measure 5 to 10 Kb. The "colors" represented here must be included/understood like probes of different nature, it can differ by the fluorochrome associated but also by their size or any other character or combination with characters—in particular it is not a question itself of fluorescent probes—. Spacing between the probes can be for example about 20 KB for small spaces, 40 KB for the large ones and less than 10 KB for the doublets (in the first case). Redundant coding is a combination of both others.

Figure 6:
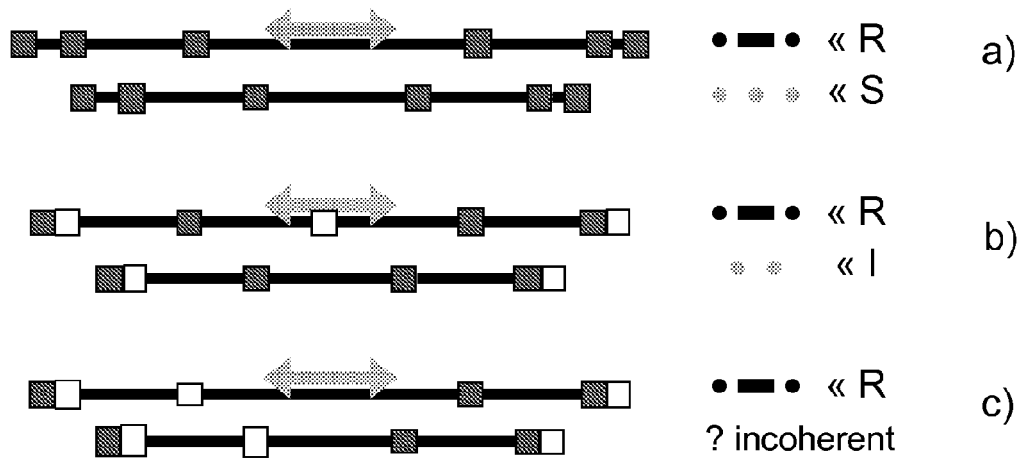

FIG. 6: shows the interest of redundant code

Interest of redundant coding. A deletion on the part of the marked sequence of a blue arrow is illustrated for the 3 types of described coding 1. In the first both cases, the modification of the reason related to the deletion involves confusion with another sequence of codes. In the third case, the sequence of codes obtained is incoherent and it thus appears clearly that there was a rearrangement. The nature of this rearrangement (a deletion) will be possibly identified according to the context.

FIG. 7: shows overlapping code

Overlapping coding. Three natures of probes are represented by the letters A, B and C. One shows in top how, by ordering the various sequence of codes made up of 7 consecutive probes so that the 6 last probes of the one correspond to the 6 first of the following, it is possible to obtain a succession of probes where any succession of 7 letters is single. In bottom, a succession of 2193 letters A, B and C, such as all the possible reasons for 7 letters are represented only once. Thus, if for example a fragment including/understanding the sequence of codes abaaccb is detected, it is known that it results from the area in red.

DETAILED DESCRIPTION

The inventors have now discovered a novel approach for the design of probes, which allows distinction of a virtually infinite number of regions, using very few probes of different nature—or even one single nature of probes. In this approach, landmarks are made of several probes which together make a symbol unique to each landmark, which is a sequence of codes one code being obtained by the reading of a succession of two probes. This motif (sequence of codes) may combine the nature and the position of probes.

This invention provides several examples of applications of this approach, one of which has been successfully used for the study of replication in one given locus. In this latter case, one single nature of probe has been used. It is also shown how it is possible, with very few different natures of probes, to landmark with a high resolution regions the size of whole chromosomes (e.g. 3 natures of probes allow to landmark 60 Mb with a 40 kb resolution).

Our invention consists in marking domains in a differentiable way by using markers of only one nature, but laid out spatially in the domain of interest so that they form a single succession of probes for each domain, which form a single sequence of codes for each domain. Because one of the possible implementations of this method consists in adapting the Morse code by using a letter (a code) by domain in a portion of genome, we gave him the code name Genetic Morse, the "dots" and "dashes" of the Morse code being replaced by markers separated respectively by short or long intervals.

It can be necessary, or more effective, to locate in an univocal way the beginning and the end of the specific sequence of codes of a domain. This location can be obtained for example by using a "doublet" of markers (extremity probes couple of start or end, said probes being labeled with markers (labels) i.e. two markers separated by an interval shorter than all those used inside the specific sequence of codes of a domain, to mark the beginning and the end of the reading of a sequence of codes. The short intervals in the "doublets" marking the beginning and the end of the sequence of codes can be of different lengths, allowing the orientation of the sequence of codes.

In a general way, our method consists in punctuating a macromolecule of landmarks made up of a certain number of markers of only one nature laid out spatially so that they form a sequence of codes specific to each landmark, the markers being directly related to the studied macromolecule.

In the case where the markers are all identical, many modes of detection of the markers are possible (autoradiography, scintillation, fluorescence, chimiluminescence, . . . ). A practically infinite number of sequences of codes, each specific of a domain, can thus be obtained, the only limit being the spatial resolution of the method used and the latitude in specific positioning of the markers.

Obviously, according to the present invention, if markers of different natures can be used, even in a limited number, the sequence of codes can be obtained by combinations of these different markers. The possibilities of coding of the landmarks are then even more numerous.

Example 1 of the present application concerns the study of a biological phenomenon (in fact DNA replication) on a precise locus delimited by these landmarks. A domain of 1.5 Mb has been marked using 4 sequences of codes, directly inspired from the Morse Code. Each one of these 4 sequences of codes is made up of 5 or 7 probes of only one nature (only one fluorochrome and identical lengths) in a variable number and spaced in a variable way, detected by fluorescence (FIG. 5 a). Each beginning of a domain of interest is marked by a separate "start extremity probe couple", each probe of said couple being spaced by 17 kb, while each ending of a domain of interest is marked by a separate "end extremity probe couple", each probe of said couple being spaced by 6 kb. The codes correspond to the first 4 letters of the Morse code, the dots consisting of probes separated by small distances (approx. 25-30 kb), the dashes by long distances (55-70 KB).

It is also possible to code the beacons while following the Code Morse by using markers of two different natures, regularly spaced (FIG. 5b). For example, in fluorescence, a specific colour can be given to the "dots" of the Morse and another specific colour for the "dashes". This method has the advantage of being more "compact", i.e. the whole sequence of code forming is contained in a sequence overall shorter, which can have advantages.

As in the preceding case, it can be wished to mark the beginning and the end of a sequence of code specific of a domain. A doublet (or couple) of two probes marked each one with a different color can be used, which can be systematically directed in the same direction. This doublet then gives the direction of reading of the sequence of code.

The two systems previously described can also be combined (FIG. 5 c): the "dots" are made of two probes of same colour separated by a short space, the "dashes" are made of two probes of different colour separated by a long space. The redundancy of the two systems of coding allows a greater robustness.

In particular in cartographic application of the invention, for example molecular diagnosis, variations of sequences are expected, which may modify the sequence of codes formed by the probes: missing or repeated or spaces between the probes modified. If one of the sequences of codes is thus modified, with only one coding system in the best case it could become impossible to decode the sequence of codes and in the worst case it could be confused with another. If the two redundant systems are used, confusion with another sequence of codes becomes far from probable, and in the best cases one can identify the sequence of codes and the sequence variation can be clearly defined (FIG. 6).

One of the advantages of the approach of the probe design described in this invention is the possibility of creating a very large number of probes with labels of few different "colors".

Some implementations highlighting this characteristic are described: thus, with 7 probes created by using only 3 colors, according to the present invention, it is possible to create 2187 ($=3^7$) different codes, with a uniform length and spacing of probes. Moreover, it is possible to order these 2187 codes so that the 6 last probes which constitute one code correspond to the 6 first probes of the following code.

If these codes are superimposed, it is possible to obtain a succession of 2193 probes in which 7 consecutive probes define a unique code, therefore a unique site on the sequence on which these probes are placed, and therefore a specific domain of interest on the macromolecule.

Thus it is possible for example to mark up more than 100 Mb while placing a probe every 50 kb (for example 5 kb-probes, in three colors or pseudo-colors). The original position (position in the 100 Mb-sequence) of each DNA fragment on which it will be possible to detect at least 7 probes (thus all fragments of more than 400 kb) will be clearly identified. The sequence in FIG. 7, composed of 3 letters A, B and C corresponding to 3 colors of probes totals 2193 letters and each succession of 7 letters is single.

The advantages of this implementation are on the one hand that it optimizes the relationship between the number of probes, the resolution and the proportion of the exploitable fragments (i.e. those which can be relocated in an unambiguous way in the total sequence) and on the other hand that this implementation is easily automatable, the succession of the probes being easy to find by data processing.

A solution with the problem of orientation of the fragments of symmetrical sequences is periodically to introduce (for example every 7 probes) an "orientated" probe into the succession of probes described above regardless of symmetry. For example, it is possible to replace every $7^{th}$ probe by a doublet which gives at the same time the "color" of the probe and its orientation. A doublet would be made of two closely spaced probes. It is thus possible to replace an "A" by an "AB" doublet, a "B" by a "BC" doublet and "C" by a "CA" doublet.

There are numerous advantages to the present invention. Indeed, in the prior art, development efforts so far consisted in multiplying the number of different detectable elements. In particular, this lead to use fluorescence detection as the main detection method, because only fluorescence allows to use many different colors to tag probes. In this context, using a limited set of colors allows to significantly reduce acquisition and analysis times. Moreover, the possibility of keeping only one or two different detectable elements allows for the use of much faster and more easily automatable detection techniques. Lastly, even for fluorescence detection the number of different possible natures of probes remains limited, whereas our method allows to generate a virtually infinite number of landmarks.

Consequently, in one aspect the present invention relates to a method of detection of the presence and/or the position of at least one domain of interest on a macromolecule to test, wherein said method comprises the following steps:

a) determining beforehand at least two target regions on the domain of interest, designing and obtaining corresponding labeled probes of each target region, named set of probe of the domain of interest, the position of these probes one compared to the others being chosen and forming the specific signature of said domain of interest on the macromolecule to test;

b) after spreading of the macromolecule to test on which the probes obtained in step a) are bound, detection of the position one compared to the others of the probes bound on the linearized macromolecule, the detection of the signature of a domain of interest indicating the presence of said domain of interest on the macromolecule to test, and conversely the absence of detection of signature or part of signature of a domain of interest indicating the absence of said domain or part of said domain of interest on the macromolecule to test.

The position of these probes one compared to the others being chosen arbitrarily and specifically to form the specific signature of said domain of interest on the macromolecule to test.

By arbitrarily it is meant according to the present invention that the man state in the art can chose the position of the probes on the domain of interest, in a way independent of any conditions, in particular the domain sequence.

By specifically it is meant according to the present invention that the man skilled in the art can chose the position of the probes on the domain of interest, in a way to form a specific signature of the domain of interest, that permit the determination of its presence or absence on the macromolecule. This signature is chosen by the man skilled in the art, the only condition being to attribute different signatures for different domains of interest.

The spacing (or gaps) between two consecutives signals is measured by direct measurement if e.g. microscopy or autoradiography is used, or any other suitable method, depending on the detection method.

In an embodiment, the detection of the presence of a domain of interest can be a detection of partial signature, for example with one or more probes missing, or binding at a wrong position (for example with a larger or smaller spacing with its consecutive probe on the domain of interest) this partial signature being the indication of an alteration of the domain of interest on the macromolecules. In the case of macromolecule being DNA, this alteration can be a mutation such as a deletion, insertion or substitution of one or several nucleotides on the domain of interest on the macromolecule.

In an embodiment, the method is preferably for determination of the presence and/or position of at least two domains of interest and comprising in step a) determining beforehand at least three target regions on the domain of interest.

In an embodiment, the signature of a domain of interest according to the present invention results from the succession of spacing between consecutive probes.

In an embodiment the position of the domain of interest according to the present invention is used as reference to locate a chemical or a biochemical reaction.

In an embodiment, the position of the domain of interest according to the present invention is used to establish a physical map in the macromolecule encompassing the target region.

In an embodiment, the signature of the domain of interest according to the present invention consist in a succession of different labelled probes.

In an embodiment, some of the probe of the target region according to the present invention are also part of the signature of at least one other the domain of interest located near on the macromolecule.

In an embodiment, the macromolecule is nucleic acid, protein, polymer, or carbohydrate. Particularly the macromolecule is DNA, double-stranded DNA or single stranded DNA, more particularly double-stranded DNA in the case of molecular combing is used for linearization of the DNA.

As used interchangeably herein, the terms "oligonucleotides", "nucleic acids" and "polynucleotides" include RNA, DNA, or RNA/DNA hybrid sequences of more than one nucleotide in either single chain or duplex form.

As used herein, the term "nucleic acids" and "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. Throughout the present specification, the expression "nucleotide sequence" may be employed to designate indifferently a polynucleotide or a nucleic acid. More precisely, the expression "nucleotide sequence" encompasses the nucleic material itself and is thus not restricted to the sequence information (i.e. the succession of letters chosen among the four base letters) that biochemically characterizes a specific DNA or RNA molecule. Also, used interchangeably herein are terms "nucleic acids", "oligonucleotides", and "polynucleotides".

In the case of the macromolecules being DNA single strand and the probes being oligonucleotides, the term "binding" means "hybridizing".

As used herein, the term "hybridization", "hybridizes to" or "hybridizing" is intended to describe conditions for moderate stringency or high stringency hybridization, preferably where the hybridization and washing conditions permit nucleotide sequences at least 60% homologous to each other to remain hybridized to each other.

Preferably, the conditions are such that sequences at least about 70%, more preferably at least about 80%, even more preferably at least about 85%, 90%, 95% or 98% homologous to each other typically remain hybridized to each other. Stringent conditions are known to those skilled in the art and can be found in Current Protocols in Molecular Biology, John Wiley & Sons, N.Y. (1989), 6.3.1-6.3.6.

By nucleic sequences having a percentage of identity of at least 80%, preferably 85%, 90%, 95% and 98%, after optimum alignment with a preferred sequence, it is intended to indicate the nucleic sequences having, with respect to the reference nucleic sequence, certain modifications such as, in particular, a deletion, a truncation, an elongation, a chimeric fusion and/or a substitution, especially point substitution. It preferably concerns sequences in which the sequences code for the same amino acid sequences as the reference sequence, this being connected to the degeneracy of the genetic code, or complementary sequences which are capable of hybridizing specifically with the reference sequences, preferably under conditions of high stringency, especially such as defined below.

A hybridization under conditions of high stringency signifies that the temperature conditions and ionic strength conditions are chosen in such a way that they allow the maintenance of the hybridization between two fragments of complementary DNA. By way of illustration, conditions of high stringency of the hybridization step for the purposes of defining the polynucleotide fragments described above are advantageously the following.

The DNA-DNA or DNA-RNA hybridization is carried out in two steps: (1) prehybridization at 42° C. for 3 hours in phosphate buffer (20 mM, pH 7.5) containing 5× SSC (1× SSC corresponds to a 0.15 M NaCl+0.015 M sodium citrate solution), 50% of formamide, 7% of sodium dodecyl sulfate (SDS), 10× Denhardt's, 5% of dextran sulfate and 1% of salmon sperm DNA; (2) actual hybridization for 20 hours at a temperature dependent on the size of the probe (i.e.: 42° C., for a probe size>100 nucleotides) followed by 2 washes of 20 minutes at 20° C. in 2× SSC+2% of SDS, 1 wash of 20 minutes at 20° C. in 0.1× SSC+0.1% of SDS. The last wash is carried out in 0.1× SSC+0.1% of SDS for 30 minutes at 60° C. for a probe size>100 nucleotides. The hybridization conditions of high stringency described above for a polynucleotide of defined size can be adapted by the person skilled in the art for oligonucleotides of greater or smaller size, according to the teaching of Sambrook et al., (1989, Molecular cloning: a laboratory manual. 2nd Ed. Cold Spring Harbor).

In an embodiment, the probes are oligonucleotides of at least 15 nucleotides, preferably at least 1 Kb more preferably between 1 to 10 kb, even more preferably between 4 to 10 kb.

Since maximal resolution on combed DNA is 1-4 kb, probes according to present invention are preferably of at least 4 kb.

In an embodiment, linearization of the macromolecule is made before or after binding of the probes on the macromolecules.

In an embodiment, the linearization of the macromolecule is made by molecular combing or Fiber Fish.

Molecular combing is done according to published methods (Lebofsky and Bensimon, 2005). Physical characterization of single genomes over large genomic regions is possible with molecular combing technology. An array of combed single DNA molecules is prepared by stretching molecules attached by their extremities to a silanised glass surface with a receding air-water meniscus. By performing fluorescent hybridization on combed DNA, genomic probe position can be directly visualized, providing a means to construct physical maps and for example to detect micro-rearrangements. Single-molecule DNA replication can also be monitored through fluorescent detection of incorporated nucleotide analogues on combed DNA molecules.

FISH (Fluorescent in situ hybridization) is a cytogenetic technique which can be used to detect and localize DNA sequences on chromosomes. It uses fluorescent probes which bind only to those parts of the chromosome with which they show a high degree of sequence similarity. Fluorescence microscopy can be used to find out where the fluorescent probe bound to the chromosome.

In FISH process, first, a probe is constructed. The probe has to be long enough to hybridize specifically to its target (and not to similar sequences in the genome), but not too large to impede the hybridization process, and it should be tagged directly with fluorophores, with targets for antibodies or with biotin. This can be done in various ways, for example nick translation and PCR using tagged nucleotides. Then, a chromosome preparation is produced. The chromosomes are firmly attached to a substrate, usually glass. After preparation the probe is applied to the chromosome DNA and starts to hybridize. In several wash steps all unhybridized or partially hybridized probes are washed away. If signal amplification is necessary to exceed the detection threshold of the microscope (which depends on many factors such as probe labelling efficiency, the kind of probe and the fluorescent dye), fluorescent tagged antibodies or streptavidin are bound to the tag molecules, thus amplifying the fluorescence. Finally, the sample is embedded in an anti-bleaching agent and observed on a fluorescence microscope.

In fiber FISH, interphase chromosomes are attached to a slide in such a way that they are stretched out in a straight line, rather than being tightly coiled, as in conventional FISH, or adopting a random conformation, as in interphase FISH. This is accomplished by applying mechanical shear along the length of the slide; either to cells which have been fixed to the slide and then lysed, or to a solution of purified DNA. The extended conformation of the chromosomes allows dramatically higher resolution—even down to a few kilobases. However, the preparation of fiber FISH samples, although conceptually simple, is a rather skilled art, meaning only specialised laboratories are able to use it routinely.

A protocol of Fiber Fish method is described above:
Equipment and Reagents:
lymphoblastoid cell culture
PBS
Haemocytometer
lysis solution
5 parts 70 mM NaOH, 2 parts absolute ethanol (Fidlerova et al. 1994). This solution can be stored at RT for several months.
Method
Take 1-2 ml of cell suspension from a healthy culture.
Wash twice in 5 ml PBS.
Re-suspend in 1 ml PBS.
Count an aliquot of cells using the haemocytometer.
Dilute cells with additional PBS to give a final concentration of approximately 2×106/ml.
Spread 10 µl of cell suspension over a 1 cm area on the upper part of a clean microscope slide.
Air dry.
Fit a slide into a plastic Cadenza (Shandon Southern) chamber and clamp in a nearly vertical position.
Apply 150 µl of lysis solution into the top of the cadenza.
As the level drops below the frosted edge of the slide, add 200 µl of ethanol.
Allow to drain briefly.
Holding the edges, carefully lift the slide and cadenza unit out of the clamp.
Pull the top of the slide back from the cadenza, allowing the meniscus to move down the slide.

Air dry at an angle.

Fix in acetone for 10 minutes. Slides can be stored satisfactorily at room temperature for several months.

In an embodiment, all the probes are labelled with the same label.

In an embodiment the probes are labelled with at least two different labels. In an embodiment, the probes are labelled with three labels.

In an embodiment, the bound or hybridized probes are detected by detecting one or more labels attached to the probes. The labels may be incorporated by any of a number of means well known to those of skill in the art. However, in a preferred embodiment, the label is simultaneously incorporated during the amplification step in the preparation of the probes. For example, polymerase chain reaction (PCR) with labeled primers or labeled nucleotides will provide a labeled amplification product. The probe (e.g., DNA) is amplified in the presence of labeled deoxynucleotide triphosphates (dNTPs).

In a preferred embodiment, transcription amplification, as described above, using a labelled nucleotide (e.g. fluorescein-labeled UTP and/or CTP) incorporates a label into the transcribed nucleic acids.

Alternatively, a label may be added directly to the original probe (e.g., mRNA, polyA mRNA, cDNA, etc.) or to the amplification product after the amplification is completed. Such labelling can result in the increased yield of amplification products and reduce the time required for the amplification reaction. Means of attaching labels to probes include, for example nick translation or end-labeling (e.g. with a labeled RNA) by kinasing of the nucleic acid and subsequent attachment (ligation) of a nucleic acid linker joining the probe to a label (e.g., a fluorophore).

Preferably, labeled nucleotide according to the present invention are Chlorodeoxyuridine (CldU), Bromoeoxyuridine (BrdU) and or Iododeoxyuridine (IdU).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oreg., USA), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is preferred because it provides a very strong signal with low background. It is also optically detectable at high resolution and sensitivity through a quick scanning procedure.

The probe can all be labeled with a single label, e.g., a single fluorescent label. Alternatively, in another embodiment, different probes can be simultaneously hybridized where each probe has a different label. For instance, one target could have a green fluorescent label and a second target could have a red fluorescent label. The scanning step will distinguish sites of binding of the red label from those binding the green fluorescent label. Each probe (target nucleic acid) can be analyzed independently from one another.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescers.

A wide variety of suitable dyes are available, being primarily chosen to provide an intense color with minimal absorption by their surroundings. Illustrative dye types include quinoline dyes, triarylmethane dyes, acridine dyes, alizarine dyes, phthaleins, insect dyes, azo dyes, anthraquinoid dyes, cyanine dyes, phenazathionium dyes, and phenazoxonium dyes.

A wide variety of fluorescers can be employed either alone or, alternatively, in conjunction with quencher molecules. Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes. oxacarbocyanine, marocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidzaolylphenylamine, 2-oxo-3-chromen, indole, xanthen, 7-hydroxycoumarin, phenoxazine, salicylate, strophanthidin, porphyrins, triarylmethanes and flavin.

Individual fluorescent compounds which have functionalities for linking or which can be modified to incorporate such functionalities include, e.g., dansyl chloride; fluoresceins such as 3,6-dihydroxy-9-phenylxanthhydrol; rhodamineisothiocyanate; N-phenyl 1-amino-8-sulfonatonaphthalene; N-phenyl 2-amino-6-sulfonatonaphthalene: 4-acetamido-4-isothiocyanato-stilbene-2,2'-disulfonic acid; pyrene-3-sulfonic acid; 2-toluidinonaphthalene-6-sulfonate; N-phenyl, N-methyl 2-aminonaphthalene-6-sulfonate; ethidium bromide; stebrine; auromine-0,2-(9'-anthroyl) palmitate; dansyl phosphatidylethanolamine; N,N'-dioctadecyl oxacarbocyanine; N,N'-dihexyl oxacarbocyanine; merocyanine, 4(3'pyrenyl)butyrate; d-3-aminodesoxy-equilenin; 12-(9'anthroyl)stearate; 2-methylanthracene; 9-vinylanthracene; 2,2'(vinylene-p-phenylene)bisbenzoxazole; p-bis [2-(4-methyl-5-phenyl-oxazolyl)]benzene; 6-dimethylamino-1,2-benzophenazin; retinol; bis(3'-aminopyridinium) 1,10-decandiyl diiodide; sulfonaphthylhydrazone of hellibrienin; chlorotetracycline; N(7-dimethylamino-4-methyl-2-oxo-3-chromenyl)maleimide; N-[p-(2-benzimidazolyl)-phenyl]maleimide; N-(4-fluoranthyl)maleimide; bis (homovanillic acid); resazarin; 4-chloro-7-nitro-2,1,3benzooxadiazole; merocyanine 540; resorufin; rose bengal; and 2,4-diphenyl-3(2H)-furanone.

In particular fluorescent labels according to the present invention are 1-Chloro-9,10-bis(phenylethynyl)anthracene, 5,12-Bis(phenylethynyl)naphthacene, 9,10-Bis(phenylethynyl)anthracene, Acridine orange, Auramine O, Benzanthrone, Coumarin, 4',6-Diamidino-2-phenylindole (DAPI), Ethidium bromide, Fluorescein, Green fluorescent protein, Hoechst stain, Indian Yellow, Luciferin, Phycobilin, Phycoerythrin, Rhodamine, Rubrene, Stilbene, TSQ, Texas Red, and Umbelliferone.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

According to the present invention, when the labelling is made with fluorescent label, the reading of signals is made by fluorescent detection the fluorescently labelled probe is excited by light and the emission of the excitation is then detected by a photosensor such as CCD camera equipped which appropriate emission filters which captures a digital image and allows further data analysis.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. A diverse number of families of compounds have been found to provide chemiluminescence under a variety or conditions. One family of compounds is 2,3-dihydro-1,-4-phthalazinedione. The must popular compound is luminol, which is the 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence can also be obtained with oxalates, usually oxalyl active esters, e.g., p-nitrophenyl and a peroxide, e.g., hydrogen peroxide, under basic conditions. Alternatively, luciferins can be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label may be added to the probe (or target, which is in particular nucleic acid(s)) prior to, or after the hybridization. So called "direct labels" are detectable labels that are directly attached to or incorporated into the probe prior to hybridization. In contrast, so called "indirect labels" are joined to the hybrid duplex after hybridization. Often, the indirect label is attached to a binding moiety that has been attached to the probe prior to the hybridization. Thus, for example, the probe may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see Laboratory Techniques in Biochemistry and Molecular Biology, Vol. 24: Hybridization With Nucleic Acid Probes, P. Tijssen, ed. Elsevier, N.Y., (1993)).

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends.

As shown for example herein, labels can be attached at positions on the ribose ring or the ribose can be modified and even eliminated as desired. The base mioeties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

Concerning end-labeling probes, in many applications it is useful to directly label probes without having to go through amplification, transcription or other conversion step. In general, end-labeling methods permit the optimization of the size of the nucleic acid to be labeled. End-labeling methods also decrease the sequence bias sometimes associated with polymerase-facilitated labeling methods. End labeling can be performed using terminal transferase (TdT).

End labeling can also be accomplished by ligating a labeled oligonucleotide or analog thereof to the end of a probe. Other end-labeling methods include the creation of a labeled or unlabeled "tail" for the nucleic acid using ligase or terminal transferase, for example. The tailed nucleic acid is then exposed to a labeled moiety that will preferentially associate with the tail. The tail and the moiety that preferentially associates with the tail can be a polymer such as a nucleic acid, peptide, or carbohydrate. The tail and its recognition moiety can be anything that permits recognition between the two, and includes molecules having ligand-substrate relationships such as haptens, epitopes, antibodies, enzymes and their substrates, and complementary nucleic acids and analogs thereof.

The labels associated with the tail or the tail recognition moiety includes detectable moieties. When the tail and its recognition moiety are both labelled, the respective labels associated with each can themselves have a ligand-substrate relationship. The respective labels can also comprise energy transfer reagents such as dyes having different spectroscopic characteristics. The energy transfer pair can be chosen to obtain the desired combined spectral characteristics. For example, a first dye that absorbs at a wavelength shorter than that absorbed by the second dye can, upon absorption at that shorter wavelength, transfer energy to the second dye. The second dye then emits electromagnetic radiation at a wavelength longer than would have been emitted by the first dye alone. Energy transfer reagents can be particularly useful in two-colour labeling schemes such as those set forth in a copending U.S. patent application, filed Dec. 23, 1996, and which is a continuation-in-part of U.S. Ser. No. 08/529,115, filed Sep. 15, 1995, and Int'l Appln. No. WO 96/14839, filed Sep. 13, 1996, which is also a continuation-in-part of U.S. Ser. No. 08/670,118, filed on Jun. 25, 1996, which is a division of U.S. Ser. No. 08/168,904, filed Dec. 15, 1993, which is a continuation of U.S. Ser. No. 07/624,114, filed Dec. 6, 1990. U.S. Ser. No. 07/624,114 is a CIP of U.S. Ser. No. 07/362,901, filed Jun. 7, 1990, incorporated herein by reference.

In an embodiment, when the labeling is made with radioactive label, the reading of signals is made by radioactive detection.

Radioactive detection of can be made with X-ray. film or a phosphorimager.

Examples of radioactive labels according to the present invention are.$^3$ H, $^{125}$ I, $^{35}$ S., $^{14}$ C, or .$^{32}$ P.

In a preferred embodiment the probes are labeled with fluorescent label.

In a preferred embodiment the probes are labeled with radioactive label.

According to the present invention, in the case of the probes are labeled with at least two different labels the signature of a domain of interest results of the succession of labels.

In an embodiment the binding of at least three probes corresponding to a domain of interest on the macromolecule forms a sequence of at least two spaces chosen between a group of at least two different spaces (for example "short" and "large"), said group being identical for each domain of interest.

In an embodiment the set of probes comprises in addition two probes (probe 1 or probe 2), each probe capable of binding on a different extremity of the domain of interest, the reading of the signal of one of said probe 1 or probe 2 associated with its consecutive probe in the domain of interest, named "extremity probe couple of start or end" allowing to obtain an information of start or end of reading.

In an embodiment the information of start of reading results of the reading of the spacing between the two consecutives probes of the extremity probe couple of start.

In an embodiment the information of end of reading results of the reading of the spacing between the two consecutives probes of the extremity probe couple of end.

In an embodiment the information of start of reading results of the reading of the spacing between the two consecutives probes of the extremity probe couple of start and the information of end of reading results of the reading of the spacing between the two consecutives probes of the extremity probe couple of end, said spacing being different for the extremity probe couple of start and the extremity probe couple of end in order to differentiate information of start and end.

Another aspect of the invention concerns a method of determination of the presence of at least one domain of interest on a macromolecule, a set of at least three probes capable of binding specifically on said domain being designed wherein the binding of one set of at least three probes on the macromolecule forms a sequence of at least two codes chosen between a group of at least two different codes (for example "dots" and "dashes"), said group being identical for each domain, said sequence of codes being specific of the domain and being the signature of the domain, and said method comprising the following steps:
  a) contacting said at least two sets of at least three probes with the macromolecule, each set being specific of each domain of interest;
  b) reading of signals, one signal corresponding of one probe;
  c) transcription of said signals in codes;
  d) detection of the presence or not of a sequence of codes specific of the domain of interest, the presence of said sequence of codes corresponding to the presence and indicating the position of the domain on the macromolecule;
and optionally a step of linearization of the macromolecule before step a) or between step a) and b).

In a preferred embodiment, a method is for the determination of the presence of at least two domains of interest on a macromolecule.

In a preferred embodiment, the code obtained results of the reading of the characteristic of two consecutives signals.

In an embodiment, the characteristic of two consecutives signals is given by a labeling of the probes.

In an embodiment, the labeling is made with fluorescent label, a specific fluorescent label corresponding to a specific code.

In an embodiment, the labeling is made with radioactive label, a specific radioactive label corresponding to a specific code.

In an embodiment, the code obtained results of the reading of the spacing between two consecutives signals.

In an embodiment, a particular spacing between two signals corresponds to a particular code.

For example, according to the present invention, small gaps correspond to a code named dots and large gaps to a code named dashes. Small codes can be designed to measure for example 25-30 kb and large codes can be designed to measure for example 55-70 kb.

In an embodiment, the characteristic of two consecutives signals is given by the length of the probes, each length corresponding to a specific code.

It is obvious that the invention is not reduce to two codes, but can comprise three, four or more than four codes, any size of gap can be chosen to define a code, said sizes being arbitrary.

According to the present invention, the set of probes comprises in addition two probes (probe 1 or probe 2), each probe capable of binding on a different extremity of the domain of interest, the reading of the signal of one of said probe 1 or probe 2 associated with its consecutive probe in the domain of interest, named "extremity probe couple of start or end" allowing to obtain an information of start or end of reading.

In an embodiment, the signature according to the present invention comprises a space between the first and the second probe in a set of probes, the space being different from all other spaces in the signature and the space can be used to obtain information about the start of the signature.

In an embodiment, the signature according to the present invention comprises a space between the next to last and the last probe in a set of probes, the space being different from all other spaces in the signature and the space can be used to obtain information about the end of the signature.

In an additional embodiment, the invention relates to a kit for the detection of the presence of at least two domain of interest on a macromolecule comprising at least two set of three probes, each set of probes being capable of binding specifically on one domain wherein the binding of one set of at least three probes on the macromolecule forms a sequence of at least two codes chosen between a group of at least two different codes (for example "dots" and "dashes"), said group being identical for all the domains, said sequence of codes being specific of one domain and being the signature of said domain.

The present invention will be understood more clearly on reading the description of the experimental studies performed in the context of the research carried out by the applicant, which should not be interpreted as being limiting in nature.

EXAMPLE

Mammalian DNA replication origins localize to sites that range from bps to tens of kbs. A regular distribution of initiations in individual cell cycles suggests that only a limited number of these numerous potential start sites are converted into activated origins. Origin interference can silence redundant origins; however, it is currently unknown whether interference participates in spacing functional human initiation events. By using a novel hybridization strategy, Genomic Morse Code, on single combed DNA molecules from primary keratinocytes, the inventors report the initiation sites present on 1.5 Mb of human chromosome 14q11.2. The inventors confirm that initiation zones are widespread in human cells. Origins used in individual cell cycles are less abundant than the potential sites of initiation and their limited use produces regular inter-origin firing distances.

Between-zone interference decreases in proportion to the distance from the active origin, while within-zone interference is 100% efficient. These results identify a hierarchical organization of origin activity in human cells. Functional origins govern the probability that nearby origins will fire, which is mediated by between- and within-zone interference. This ensures an even distribution of initiation events along the length of human chromosomes in the context of multiple and complex potential start sites of DNA replication.

Introduction

Eukaryotic cells have a limited amount of time, defined by the length of S-phase, to duplicate their genomes. This is achieved by synthesizing DNA at replication forks, which extend from multiple sites of initiation. Since fork speed is not scaled according to S-phase length, regulating the frequency of initiation along each respective chromosome is required to prevent unreplicated gaps prior to the onset of mitosis (Hand and Tamm, 1973; Edenberg and Huberman, 1975). Although there are exceptions, the common view is that somatic mammalian origins fire at 50-300 kb intervals (Edenberg and Huberman, 1975; Berezney et al., 2000). This suggests that Metazoa do possess a mechanism to evenly distribute initiation events. Placing strong replicator sequences at regular distances is one such mechanism that is employed by the budding yeast, *Saccharomyces cerevisiae* (Newlon et al., 1991; Shirahige et al., 1993). In higher eukaryotes, genetic elements play a role in origin activation; however, they are not sufficient by themselves to drive initiation (Gilbert, 2004). Furthermore, while some Metazoan origins localize to well circumscribed sites of a few bps, a large number localize to more disperse initiation zones ranging up to tens of kbs (DePamphilis, 1999). This raises the problem of how to achieve a regular distribution of activated origins from a range of potential sites that possess low intrinsic efficiency.

One method to regulate origin activity is to change the probability it will be replicated passively. As an elongating fork from an origin neighbor mediates this suppression, this form of origin de-activation has been termed "origin interference" (Brewer and Fangman, 1993). Most of our understanding concerning origin interference has been provided by work in *S. cerevisiae*. In budding yeast, there are many more assembled pre-Replicative Complexes (pre-RCs) than those that are either needed or used to complete replication (Dershowitz and Newlon, 1993; Raghuraman et al., 2001; Wyrick et al., 2001; Pasero et al., 2002). Analysis of origin efficiency on yeast chromosomes III and VI, revealed that origins are used between 5-90% of cell cycles (Friedman et al., 1997; Yamashita et al., 1997; Poloumienko et al., 2001). Licensed origins are inefficient due to their scheduled timing late in S-phase or relatively late compared to other origins in the vicinity (Santocanale and Diffley, 1996; Vujcic et al., 1999). As a consequence, these competent origins are replicated passively by forks that elongate from flanking initiation sites (Santocanale et al., 1999).

According to data from yeast, if origins are to interfere with one another, origin neighbors must be pre-programmed in G1 to fire at different times during S-phase (Raghuraman et al., 1997). This requirement, however, may not be satisfied in higher eukaryotes, where 1) timing control is exerted over extended regions of ~100 kb (MacAlpine et al., 2004; Norio et al., 2005) and 2) origins situated next to each other fire simultaneously in clusters (Berezney et al., 2000). Indeed, at the amplified AMPD2 locus of CHO cells, significant pre-defined timing differences between nearby origins was not observed (Anglana et al., 2003). Nevertheless co-activation of adjacent origins at well-defined bp locations was blocked (Anglana et al., 2003). Whether this applies to broad initiation zones remains to be determined.

To understand how regular initiation intervals are achieved in human cells and whether origin interference contributes to this process, the inventors queried a 1.5 Mb region of human chromosome 14q11.2 from primary keratinocytes for origin activity. A single molecule approach exploiting molecular combing technology was chosen for the following reasons. Firstly, sufficient origin firing events can be obtained to position all the potential start sites of DNA replication in a particular cell type. Secondly, the inventors could determine which origins single cells use in individual S-phases and their activation timing with respect to each other. This is required to ascertain the spatio-temporal distribution of initiation events. These data were combined to evaluate whether origins that have already fired regulate downstream potential initiation site usage. Inventors found that origins self-regulate one another according to a hierarchy established by the active origin, which is selected stochastically without pre-defined timing preferences. Furthermore, origin interference yields conserved initiation event spacing. The reasons for and the mechanisms used to implement human origin interference are discussed.

Materials and Methods

DNA Preparation

Normal human primary keratinocytes were derived from skin biopsies. Cells were cultured in standard keratinocyte SFM. Thereafter, nascent DNA was labelled with IdU and CldU for 20 min each as described (Lebofsky and Bensimon, 2005). DNA extraction and combing were done according to standard protocols.

Hybridization and Fluorescent Revelation

The 25 GMC probes were produced by long-range PCR using primer pairs listed in Table S1. To help amplify 5-7 kb probes, TaKaRa LA Taq was used (Takara Bio). BACs that served as templates for PCR products are found in Table S2. Probes were pooled at a final concentration of ~20 ng/μl according to their symbol (A, B, C, and D). Biotinylation of probes was achieved by random priming (Invitrogen) the four symbols separately. For individual slide assays, ~250 ng of each biotinylated probe was combined with 10 μg of Human cot-1 DNA (Gibco BRL). After that, hybridization on combed DNA conformed to published methods (Lebofsky and Bensimon, 2005). The immunofluorescent steps to detect probes, IdU and CldU were as follows: (i) Alexa 488 conjugated streptavidin (Molecular Probes), mouse anti-bromodeoxyuridine (Becton Dickinson), and rat anti-bromodeoxyuridine (Harlan Seralab); (ii) biotin conjugated rabbit antistreptavidin(Rockland), Alexa 350 conjugated goat anti-mouse (Molecular Probes), and Texas Red conjugated donkey anti-rat (Jackson); (iii) Alexa 488 conjugated streptavidin (Molecular Probes) and Alexa 350 conjugated donkey anti-goat (Molecular Probes). Antibody incubations, washes, and slide mounting were performed as previously reported (Lebofsky and Bensimon, 2005).

Image Acquisition

Half of the images were captured with a Zeiss Axioplan 2 microscope equipped with an HQ CCD camera (Photometrics). The other half was acquired using the Cytoscout high-throughput scanning device (Upper Austrian Research). Background fluorescent dots were removed using Photoshop (Adobe) to highlight the molecule of interest.

Results

Genomic Morse Code Hybridization Strategy

As a first step towards analyzing which origins are active and silent within a given cell cycle, all potential initiation sites within a region were obtained. For this purpose, the inventors used a single molecule approach based on molecular combing (Bensimon et al., 1994). Asynchronous human primary keratinocytes displaying a normal karyotype were given 20 min pulses of iododeoxyuridine (IdU) followed by chlorodeoxyuridine (CldU). DNA from this cell population was extracted and combed. The incorporation of the BrdU analogues along newly synthesized DNA was visualized by immunological detection of IdU in blue and CldU in red. This experimental paradigm gives rise to three types of signals from which the start site of bi-directional replication can be inferred (FIG. 1A; for a detailed description, see Anglana et al., 2003; Lebofsky and Bensimon, 2005). By combining BrdU revelation with FISH, initiation can be attributed to specific sequence tracts wherever replication tracts overlap with probe signals.

Conventionally, probe pairs of either different colors (FIG. 1B*i*) or different sizes (FIG. 1B*ii*) are used to visualize a genomic region on the slide. DNA breakage, however, limits the distance they can cover. As a result, walking down a chromosome using this hybridization strategy is a time-consuming process as experiments increase proportionally to the number of probe pairs. Ideally, one could use several colors and/or probes of varying lengths to cover a large region; however, these strategies are not suitable due to spectral overlap and non-specific hybridization of repetitive sequences respectively.

The first part of our unique solution came with the realization that gaps of different size provide the same information as probes of different color or size. In the example provided in FIG. 1B*iii*, gap 1 is defined by one probe set and gap 2 is defined by another probe set. Also, the gap size between the two probe sets is distinct from gaps 1 and 2. Gap 3 becomes useful during DNA breakage. With its help, the molecule can still be oriented even though the complete set of probes is not visualized (FIGS. 1B*iv* and *v*). As gaps provide positional information, their numbers are no longer limited, i.e. spectral overlap and repetitive sequences during hybridization are no longer an issue. By using gaps of different sizes, a Genomic Morse Code (GMC) covering ~1.5 Mb in human chromosome 14q11.2 was generated (FIG. 1C). The entire GMC was hybridized in individual assays and all probes were detected in green. Prior to molecular combing, DNA manipulation causes the fibres to break in random locations. Fiber size, however, was sufficient to permit the visualization of multiple symbols on individual molecules. In contrast, due to fiber breakage, occasionally only a few of the probes from a symbol were detectable. Origins were mapped whenever replication tracks denoting initiation co-localized with a decodable set of GMC probes (FIG. 1D). Thus, the novel hybridization strategy, GMC, allowed origin mapping over a large region in a limited number of experiments.

Initiation Mapping on 1.5 Mb of Human Chromosome 14q11.2

Using this experimental paradigm, the inventors detected 307 initiation events on 232 single DNA molecules in the GMC region. Data clustering was carried out to objectively establish zones of preferential initiation. First, the inventors created a hierarchical clustering tree. To achieve the best partition, the spread of data within clusters should be minimized and the separation between clusters should be maximized. These two features are called within variance (W) and between variance (B) (FIG. 2A). Hence, the desired cluster set must have small W and big B or maximal values of B-W. When the data was divided into 9, 22, and 45 clusters, relatively high B-W values were obtained (FIG. 2A). FIG. 2B shows how initiation events are partitioned according to these cluster sets. Dividing the data set into 45 clusters yields the narrowest regions of initiation. Inventors considered these 45 clusters to represent individual initiation zones (FIG. 2C). Some of these clusters contained very few initiation events, which may have been due to background noise. Therefore, only clusters with greater than three initiation events were used for subsequent analyses. In this way, 38 initiation zones were identified.

Initiation zone sizes varied between 2.6 kb (min.) to 21.6 kb (max.) with an average of 13.5+/−5.2 kb. These values fall within the range of other initiation zones reported for mammalian cells (DePamphilis, 1999). Within the zones, specific initiation sites of 1-2 kb were not observed.

This may have been due to insufficient data numbers to distinguish origin peaks. Maximal resolution on combed molecules is between 1-4 kb. Therefore, these initiation preferences may also have been smoothed out as a result of the standard deviation inherent to each origin mapped.

Alternatively, initiation zones containing scattered firing sites may be more predominant than previously thought. Our data provide target regions that can be probed with other higher resolution techniques (Todorovic et al., 2005). Accordingly, these possibilities can be discriminated.

Spatio-temporal Analysis of Activated Origin Neighbors

The inventors next turned our attention towards how initiation zones were distributed relative to one another. Measuring distances between zone centroids revealed an inter-zone average of 40.6+/−20.7 kb (min.=14.3 kb, max.=93.1 kb). This was surprising considering that inter-origin distances in mammalian cells generally range between 100-150 kb (Berezney et al., 2000). The discrepancy can be explained if only a subset of zones is activated per cell cycle. To explore this possibility, the inventors analyzed the spacing between multiple initiations on individual fibers (FIG. 3A).

Due to the single molecule level of our analysis, these origins correspond to those that are actually used by one cell in one S-phase. DNA breakage prevented the visualization of flanking origins for 173 out of the 307 initiation events observed. The remaining cases were observed in the presence of an active origin neighbor ($^{134}/_{307}$). The two nearest and the two furthest functional origins were separated by 31.4 kb and 390.8 kb respectively. Interestingly, the mean inter-origin distance was calculated as 113+/−66.4 kb (FIG. 3B). In comparison to the interzone distance (~40 kb), this result suggests that, on average, only one origin fires from out of three potential zones in a given cell cycle (FIG. 3C).

To investigate whether origins from specific zones reproducibly fired early or later with respect to one another, activation times were examined. Based on the type of replication signals indicating an origin (FIG. 1A), the time of initiation with respect to the labeling periods could be attributed. This applies to origins that fired during either the IdU or CldU pulses, which were 20 min each in duration (FIGS. 1A*ii* and *iii*). This equally applies to origins that fired before the labeling period provided that the outgoing forks could be visualized by their incorporation of the modified nucleotides (FIG. 1A*i*). For this to occur, the time of origin activation could not precede the IdU/CldU pulses by more than 20 min on average (for example, see the 2nd molecule in FIG. 3C*i*). Therefore, the window of analysis covers ~60 min in total, comprising 20 min before the pulses, 20 min during the IdU pulse, and 20 min during the CldU pulse. The inventors could find no timing preferences for any of the 38 initiation zones. Furthermore, adjacent origins did not fire at the same time (FIG. 3C). It should be noted that multiple initiations on individual fibers were detectable within the 60 min afforded by our experimental paradigm. Therefore, although precise synchrony between initiation events was not observed, the timing differences between any two activated origins are limited to approximately one hour.

Since activation times between adjacent origins were slightly staggered, potential origins in the unreplicated regions between two oncoming forks might still have been activated at some later time (for examples, see the 3rd and 5th molecules in FIG. 3C*ii*). Origins firing from these regions would yield lower inter-origin distances. The majority of adjacent origins are considered to fire within 30 min of each other (Berezney et al., 2000). Since our window of analysis is 60 min (see above paragraph), almost all origins within a cluster are predicted to be activated.

Therefore, it is unlikely that retarded origin firing would significantly alter the inter-origin distances measured.

Fork Extension Across Potential Initiation Sites

Until now, replication tracks have been used only for the purpose of inferring their start site or initiation. Their bi-directional extension into the surrounding region, however, provides another important piece of data. Signals originating from one initiation zone that overlap a flanking zone implies for the latter the prior passage of a replication fork and removal of an origin's license.

This renders the passively replicated zone refractory from firing at some later time in S-phase.

Insofar as all potential origins in human cells are licensed as they are in yeast (Santocanale and Diffley, 1996), this observation provides evidence for origin interference (FIG. 4A). For forks that extend partway into an initiation zone, zones were only considered as suppressed if the centroid was reached. The inventors used signals from elongating forks to analyze how far from an active origin interference occurs (FIG. 4B).

In total, 528 initiation zones were found to be suppressed. Their distance from the initiation site did not significantly differ when labels representing centromeric moving forks were considered (56.5+/−37.7 kb, N=266) versus labels representing telomeric moving forks (55.1+/−38.4 kb, N=262; FIG. 4C). Consequently, for the following analyses, origin interference mediated by forks moving in both directions was combined. On average, replication tracks from active origins overlapped with zones 55.8+/−38 kb away. The closest and farthest suppressed zones were located 7 kb and 284.6 kb from the functional origin respectively. These data translate into the following. The zone situated immediately next to an initiation site was suppressed 314 times. The second zone was suppressed 137 times and subsequent zones after that (three or greater) were suppressed 77 times. Together, these data based on 528 suppressed initiation zones suggest that origin interference extends for the most part over 1-2 flanking initiation zones.

In addition to between-zone interference, the inventors also analyzed within-zone interference.

Forks from an active origin extended beyond the boundaries of its own initiation zone 100% of the time (for examples, see FIG. 4B). If this form of interference is robust, the probability of more than one origin firing per initiation zone in any given cell cycle should be low. To carry out this analysis depends on our ability to discriminate short replication tracts representative of closely spaced origins in relatively small initiation zones. The maximal resolution of linear fluorescent segments on combed DNA is 1-4 kb. This complicates the visualization of multiple initiations in zones smaller than the average of 13.5 kb. For the larger initiation zones, however, observation of several origins is not limited by the resolution of molecular combing. Regardless of initiation zone size, two or more origins were never observed to fire from within the same initiation zone in individual S-phases. Therefore, in contrast to the between-zone interference that decreases with distance from the initiation event, within-zone interference is extremely efficient and does not depend on the distance forks have to travel.

Conclusion

Figure 1:
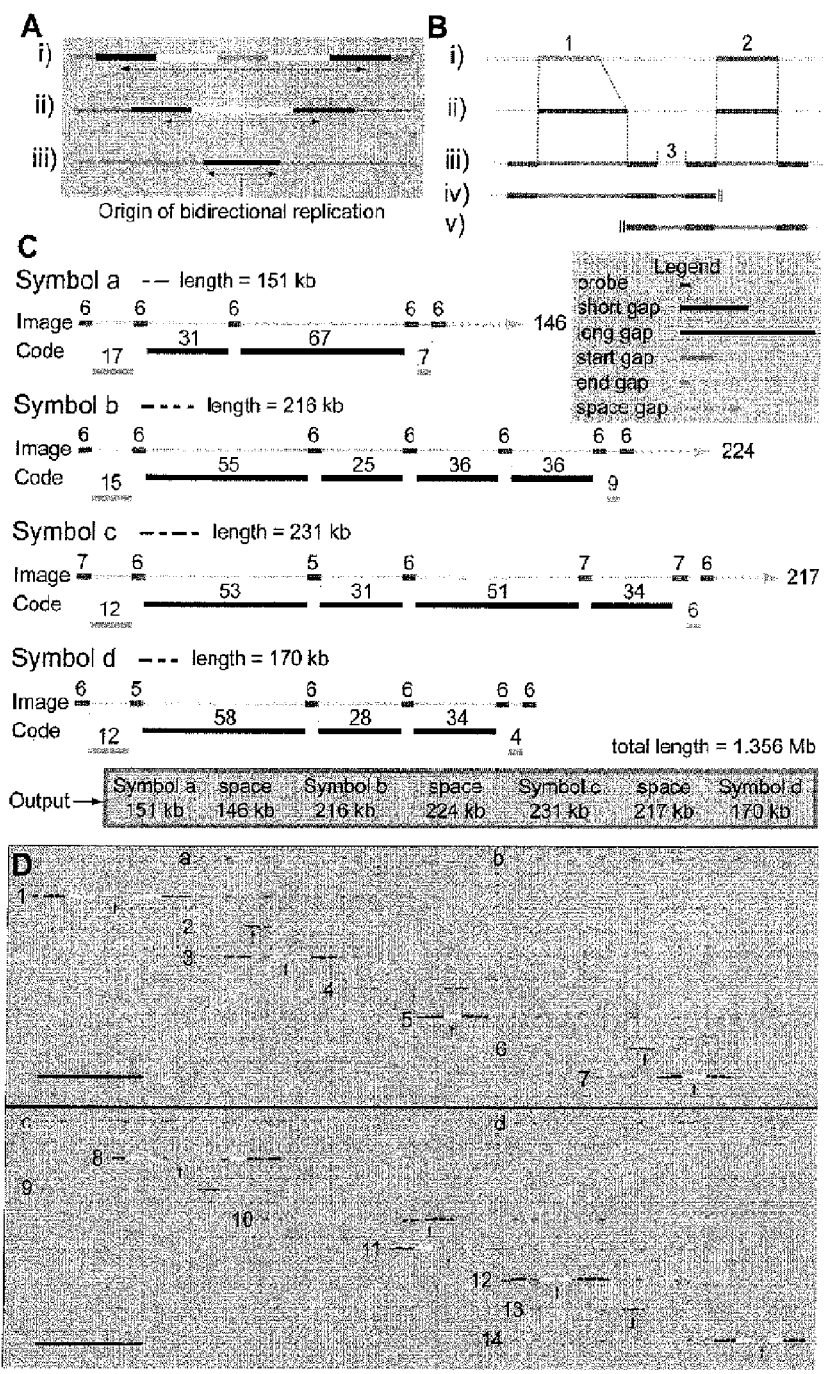
FIG. 1 shows DNA replication initiation mapping on 1.5 Mb in human chromosome 14q11.2.

In conclusion, the inventors have mapped all possible initiation zones throughout a 1.5 Mb region in human chromosome 14q11.2 using a single molecule approach (FIGS. 1 and 2). The inventors have also demonstrated that only a fraction of them are actually used in individual cell cycles (FIG. 3).

Lastly, limited origin activation yields regular inter-origin firing distances (FIG. 3).

Accordingly, the inventors show for the first time that conserved initiation event spacing is maintained in the context of broad mammalian initiation zones.

A high potential to active origin ratio has been described in yeast and CHO cells (Raghuraman et al., 2001; Wyrick et al., 2001; Pasero et al., 2002; Anglana et al., 2003). Our data suggest that this ratio is a conserved feature in human cells. This raises an important question: Why is origin redundancy a recurrent theme in eukaryotic cells? Deleting several origins on one arm of a yeast chromosome had negligible effects on genome stability (Dershowitz and Newlon, 1993). This would suggest that so many origins are not necessary.

More recently, however, it was shown that preventing the full complement of assembled pre-RC resulted in chromosomal re-arrangements (Lengronne and Schwob, 2002; Tanaka and Diffley, 2002). Although the reason for this is unknown, several proposals converge on the idea that an excess of potential origins provides a safety net in the event of perturbed DNA replication (Schwob, 2004). Firstly, if a fork is blocked, it can be converted into a substrate for recombination (Rothstein et al., 2000). Activation of a downstream "extra" origin gives rise to an oncoming fork. This fork merges with the blocked fork thereby rescuing it from recombination.

Secondly, if some origins fail to fire, cells may undergo mitosis with unreplicated DNA. This fragment will break when the centromeres are pulled apart. An oversupply of potential origins reduces the likelihood of this happening. Lastly, optimal cell-cycle arrest by the S-phase checkpoint requires a sufficient number of forks (Shimada et al., 2002). Forks are lost when an attempt to initiate fails. The firing of a backup origin generates two additional forks to compensate, thus rendering the checkpoint operational. Clearly, further work is needed to evaluate which of these models is applicable.

Origin interference has been invoked as a mechanism to explain how a high potential to active origin ratio is achieved in eukaryotes. It involves the removal of pre-RCs, which represent licensed origins, by forks progressing from earlier activated origins (Brewer and Fangman, 1993).

Origin interference has been observed in yeast, *Xenopus*, and CHO cells (Brewer and Fangman, 1993; Lucas et al., 2000; Anglana et al., 2003). Here the inventors show for the first time that origin interference plays a significant role in modulating origin function in human cells and, moreover, that this occurs in the context of initiation zones (FIG. 4). Prior to molecular combing, DNA is de-proteinated. Therefore, it was not possible to observe which of the initiation zones contained licensed origins. Indeed, passively replicated zones, which were interpreted as suppressed, may simply not have been licensed to begin with. Future work will assay pre-RC assembly amongst initiation zones. This will allow us to determine if origin interference occurs according to the canonical definition of the term.

To explain origin interference, data from yeast has been cited, whereby different activation times established in G1 causes a late origin to be passively replicated by a fork from an early origin (Lucas and Raghuraman, 2003). In agreement with work performed in CHO cells (Anglana et al., 2003), the inventors did not find any strong pre-programmed timing differences for adjacent origins (FIG. 3). Therefore, our data suggests that a mechanism different from the one present in yeast operates in human cells.

The inventors observed that between-zone interference gradually decreases with distance from the active origin (FIG. 4). If the probability of origin firing is low due to limited initiation factors (Walter and Newport, 1997), the origin interference reported here may be an indirect outcome of this low probability and, consequently, a passive phenomenon. On the other hand, if origin firing probabilities are high, origin interference must be positively regulated. For example, checkpoint proteins that are present at unperturbed elongating forks might suppress distal origins from firing.

This would actively increase the chance that delayed origins are passively replicated and, therefore, suppressed (Marheineke and Hyrien, 2004; Shechter et al., 2004; Sorensen et al., 2004; Syljuasen et al., 2005). Future research will reveal which of these models is responsible for between-zone interference.

Recently, a mathematical study proposed that only potential origins 11 kb apart can be sequestered together in a replication focus and, therefore, activated simultaneously (Jun et al., 2004). This restriction is determined by the persistence length of DNA, which limits DNA bending. Persistence length may explain within-zone interference: DNA stiffness prevents two potential initiation sites from one zone to be concentrated within a replication focus, thus preventing their simultaneous activation. The robustness of a mechanism based on the physical properties of DNA could produce the high efficiency of within-zone interference reported here.

The mechanism of origin interference within and amongst mammalian initiation zones depends upon the molecular determinants that underlie these regions. During licensing, multiple MiniChromosome Maintenance (MCM) complexes spread away from pre-RCs (Ritzi et al., 1998; Edwards et al., 2002). It has been suggested that origins firing at one of these MCM sites explain the presence of initiation zones in mammalian cells (Hyrien et al., 2003; Blow and Dutta, 2005; Cvetic and Walter, 2005). Accordingly, the initiation zones reported here (FIG. 2) may arise due to reiterative MCM loading. Determining whether diffuse MCMs or other unknown factors are responsible for mammalian initiation zones will help us understand how human origin interference is executed and initiation event spacing is regulated.

References

Anglana, M., Apiou, F., Bensimon, A., and Debatisse, M. (2003). Dynamics of DNA replication in mammalian somatic cells: nucleotide pool modulates origin choice and interorigin spacing. Cell 114, 385-394.

Bensimon, A., Simon, A., Chiffaudel, A., Croquette, V., Heslot, F., and Bensimon, D. (1994). Alignment and sensitive detection of DNA by a moving interface. Science 265, 2096-2098.

Berezney, R., Dubey, D. D., and Huberman, J. A. (2000). Heterogeneity of eukaryotic replicons, replicon clusters, and replication foci. Chromosoma 108, 471-484.

Blow, J. J., and Dutta, A. (2005). Preventing re-replication of chromosomal DNA. Nat. Rev. Mol. Cell Biol. 6, 476-486.

Brewer, B. J., and Fangman, W. L. (1993). Initiation at closely spaced replication origins in a yeast chromosome. Science 262, 1728-1731.

Cvetic, C., and Walter, J. C. (2005). Eukaryotic origins of DNA replication: could you please be more specific? Semin. Cell Dev. Biol. 16, 343-353.

DePamphilis, M. L. (1999). Replication origins in metazoan chromosomes: fact or fiction? Bioessays 21, 5-16.

Dershowitz, A., and Newlon, C. S. (1993). The effect on chromosome stability of deleting replication origins. Mol. Cell. Biol. 13, 391-398.

Edwards, M. C., Tutter, A. V., Cvetic, C., Gilbert, C. H., Prokhorova, T. A., and Walter, J. C. (2002). MCM2-7 complexes bind chromatin in a distributed pattern surrounding the origin recognition complex in Xenopus egg extracts. J. Biol. Chem. 277, 33049-33057.

Friedman, K. L., Brewer, B. J., and Fangman, W. L. (1997). Replication profile of Saccharomyces cerevisiae chromosome VI. Genes Cells 2, 667-678.

Gilbert, D. M. (2004). In search of the holy replicator. Nat. Rev. Mol. Cell Biol. 5, 848-855.

Hand, R., and Tamm, I. (1973). DNA replication: direction and rate of chain growth in mammalian cells. J. Cell Biol. 58, 410-418.

Hyrien, O., Marheineke, K., and Goldar, A. (2003). Paradoxes of eukaryotic DNA replication: MCM proteins and the random completion problem. Bioessays 25, 116-125.

Jun, S., Herrick, J., Bensimon, A., and Bechhoefer, J. (2004). Persistence length of chromatin determines origin spacing in Xenopus early-embryo DNA replication: quantitative comparisons between theory and experiment. Cell Cycle 3, 223-229.

Lebofsky, R., and Bensimon, A. (2005). DNA replication origin plasticity and perturbed fork progression in human inverted repeats. Mol. Cell. Biol. 25, 6789-6797.

Lengronne, A., and Schwob, E. (2002). The yeast CDK inhibitor Sic1 prevents genomic instability by promoting replication origin licensing in late G(1). Mol. Cell 9, 1067-1078.

Lucas, I., Chevrier-Miller, M., Sogo, J. M., and Hyrien, O. (2000). Mechanisms ensuring rapid and complete DNA replication despite random initiation in Xenopus early embryos. J. Mol. Biol. 296, 769-786.

Lucas, I. A., and Raghuraman, M. K. (2003). The dynamics of chromosome replication in yeast. Curr. Top. Dev. Biol. 55, 1-73.

MacAlpine, D. M., Rodriguez, H. K., and Bell, S. P. (2004). Coordination of replication and transcription along a Drosophila chromosome. Genes Dev. 18, 3094-3105.

Marheineke, K., and Hyrien, O. (2004). Control of replication origin density and firing time in Xenopus egg extracts: role of a caffeine-sensitive, ATR-dependent checkpoint. J. Biol. Chem. 279, 28071-28081.

Newlon, C. S., Lipchitz, L. R., Collins, I., Deshpande, A., Devenish, R. J., Green, R. P., Klein, H. L., Palzkill, T. G., Ren, R. B., Synn, S., and et al. (1991). Analysis of a circular derivative of Saccharomyces cerevisiae chromosome III: a physical map and identification and location of ARS elements. Genetics 129, 343-357.

Norio, P., Kosiyatrakul, S., Yang, Q., Guan, Z., Brown, N. M., Thomas, S., Riblet, R., and Schildkraut, C. L. (2005). Progressive activation of DNA replication initiation in large domains of the immunoglobulin heavy chain locus during B cell development. Mol. Cell 20, 575-587.

Pasero, P., Bensimon, A., and Schwob, E. (2002). Single-molecule analysis reveals clustering and epigenetic regulation of replication origins at the yeast rDNA locus. Genes Dev. 16, 2479-2484.

Poloumienko, A., Dershowitz, A., De, J., and Newlon, C. S. (2001). Completion of replication map of *Saccharomyces cerevisiae* chromosome III. Mol. Biol. Cell 12, 3317-3327.

Raghuraman, M. K., Brewer, B. J., and Fangman, W. L. (1997). Cell cycle-dependent establishment of a late replication program. Science 276, 806-809.

Raghuraman, M. K., Winzeler, E. A., Collingwood, D., Hunt, S., Wodicka, L., Conway, A., Lockhart, D. J., Davis, R. W., Brewer, B. J., and Fangman, W. L. (2001). Replication dynamics of the yeast genome. Science 294, 115-121.

Ritzi, M., Baack, M., Musahl, C., Romanowski, P., Laskey, R. A., and Knippers, R. (1998). Human minichromosome maintenance proteins and human origin recognition complex 2 protein on chromatin. J. Biol. Chem. 273, 24543-24549.

Rothstein, R., Michel, B., and Gangloff, S. (2000). Replication fork pausing and recombination or "gimme a break". Genes Dev. 14, 1-10.

Santocanale, C., and Diffley, J. F. (1996). ORC- and Cdc6-dependent complexes at active and inactive chromosomal replication origins in *Saccharomyces cerevisiae*. EMBO J. 15, 6671-6679.

Santocanale, C., Sharma, K., and Diffley, J. F. X. (1999). Activation of dormant origins of DNA replication in budding yeast. Genes Dev. 13, 2360-2364.

Schwob, E. (2004). Flexibility and governance in eukaryotic DNA replication. Curr. Opin. Microbiol. 7, 680-690.

Shechter, D., Costanzo, V., and Gautier, J. (2004). ATR and ATM regulate the timing of DNA replication origin firing. Nat. Cell Biol. 6, 648-655.

Shimada, K., Pasero, P., and Gasser, S. M. (2002). ORC and the intra-S-phase checkpoint: a threshold regulates Rad53p activation in S phase. Genes Dev. 16, 3236-3252.

Shirahige, K., Iwasaki, T., Rashid, M. B., Ogasawara, N., and Yoshikawa, H. (1993). Location and characterization of autonomously replicating sequences from chromosome VI of *Saccharomyces cerevisiae*. Mol. Cell. Biol. 13, 5043-5056.

Sorensen, C. S., Syljuasen, R. G., Lukas, J., and Bartek, J. (2004). ATR, Claspin and the Rad9- Rad1-Hus1 complex regulate Chk1 and Cdc25A in the absence of DNA damage. Cell Cycle 3, 941-945.

Syljuasen, R. G., Sorensen, C. S., Hansen, L. T., Fugger, K., Lundin, C., Johansson, F., Helleday, T., Sehested, M., Lukas, J., and Bartek, J. (2005). Inhibition of human Chk1 causes increased initiation of DNA replication, phosphorylation of ATR targets, and DNA breakage. Mol. Cell. Biol. 25, 3553-3562.

Tanaka, S., and Diffley, J. F. (2002). Deregulated G1-cyclin expression induces genomic instability by preventing efficient pre-RC formation. Genes Dev. 16, 2639-2649.

Todorovic, V., Giadrossi, S., Pelizon, C., Mendoza-Maldonado, R., Masai, H., and Giacca, M. (2005). Human origins of DNA replication selected from a library of nascent DNA. Mol. Cell 19, 567-575.

Vujcic, M., Miller, C. A., and Kowalski, D. (1999). Activation of silent replication origins at autonomously replicating sequence elements near the HML locus in budding yeast. Mol. Cell. Biol. 19, 6098-6109.

Walter, J., and Newport, J. W. (1997). Regulation of replicon size in *Xenopus* egg extracts. Science 275, 993-995.

Wyrick, J. J., Aparicio, J. G., Chen, T., Barnett, J. D., Jennings, E. G., Young, R. A., Bell, S. P., and Aparicio, O. M. (2001). Genome-wide distribution of ORC and MCM proteins in *S. cerevisiae*: high-resolution mapping of replication origins. Science 294, 2357-2360.

Yamashita, M., Hori, Y., Shinomiya, T., Obuse, C., Tsurimoto, T., Yoshikawa, H., and Shirahige, K. (1997). The efficiency and timing of initiation of replication of multiple replicons of *Saccharomyces cerevisiae* chromosome VI. Genes Cells 2, 655-665.

We claim:

1. A kit for the detection of the presence of at least two domains of interest on a macromolecule, said kit comprising at least two sets of at least three probes, wherein
    at least two of the probes within each set carry the same label,
    each set of probes is capable of binding specifically on one domain of said macromolecule;
    once bound on said domain of said macromolecule, the probes from a given set form a signature distinct from the signatures formed by probes from other sets bound on their respective domains;
    wherein the characteristics allowing the distinction of two signatures include the relative position between bound probes of a given set.

2. A kit according to claim 1, wherein said macromolecule is a nucleic acid, a protein, a polymer, or a carbohydrate.

3. A kit according to claim 2, wherein said nucleic acid is DNA, double-stranded DNA, or single-stranded DNA.

4. A kit according to claim 3, wherein at least three of the probes within each set carry the same label.

5. A kit according to claim 4, wherein at least four of the probes within each set carry the same label.

6. A kit according to claim 5, wherein at least five of the probes within each set carry the same label.

* * * * *